United States Patent
Sugiyama et al.

(10) Patent No.: US 7,729,866 B2
(45) Date of Patent: Jun. 1, 2010

(54) METHOD OF DETERMINING LEVEL OF SPECIFIED COMPONENT IN BLOOD SAMPLE AND APPARATUS FOR LEVEL DETERMINATION

(75) Inventors: Koji Sugiyama, Kyoto (JP); Takeshi Takagi, Kyoto (JP)

(73) Assignee: ARKRAY, Inc., Kyoto (JP)

(*) Notice: Subject to any disclaimer, the term of this patent is extended or adjusted under 35 U.S.C. 154(b) by 555 days.

(21) Appl. No.: 11/666,055

(22) PCT Filed: Oct. 25, 2005

(86) PCT No.: PCT/JP2005/019557
§ 371 (c)(1),
(2), (4) Date: Apr. 20, 2007

(87) PCT Pub. No.: WO2006/046538
PCT Pub. Date: May 4, 2006

(65) Prior Publication Data
US 2008/0118942 A1     May 22, 2008

(30) Foreign Application Priority Data
Oct. 28, 2004    (JP) .............................. 2004-313963

(51) Int. Cl.
*G01N 33/49* (2006.01)
*G01N 27/327* (2006.01)
*C12Q 1/26* (2006.01)

(52) U.S. Cl. ................ 702/19; 435/14; 204/403.01; 204/403.1; 204/403.11; 600/345; 600/347; 702/23

(58) Field of Classification Search .................. None
See application file for complete search history.

(56) References Cited

U.S. PATENT DOCUMENTS
5,168,046 A    12/1992    Hamamoto et al.

FOREIGN PATENT DOCUMENTS

| JP | 7-37991 | 2/1995 |
|----|---------|--------|
| JP | 9-33533 | 2/1997 |
| JP | 9-318634 | 12/1997 |
| JP | 10-108695 | 4/1998 |
| JP | 2005-148058 | 6/2005 |

OTHER PUBLICATIONS

International Search Report from corresponding PCT/JP2005/019557, mailed Dec. 6, 2005.

*Primary Examiner*—Michael Borin
*Assistant Examiner*—Soren Harward
(74) *Attorney, Agent, or Firm*—Hamre, Schumann, Mueller & Larson, P C

(57) ABSTRACT

The present invention relates to a method for measuring the concentration of a particular component in a blood sample containing blood cells based on a variable correlated with the concentration of the particular component. In the present invention, a concentration (S) in blood plasma obtained by removing blood cell components from the blood sample, a concentration (DI) in the blood sample computed by a differential method and a concentration (EP) in the blood sample computed by an equilibrium point method are expressed by a relational expression which is unrelated to the proportion of the blood cell components in the blood sample, and the concentration of the particular component is computed by using the relational expression.

9 Claims, 4 Drawing Sheets

METHOD OF DETERMINING LEVEL OF SPECIFIED COMPONENT IN BLOOD SAMPLE AND APPARATUS FOR LEVEL DETERMINATION

TECHNICAL FIELD

The present invention relates to a technique for measuring the concentration of a particular component (e.g. glucose) in a blood sample containing blood cells.

BACKGROUND ART

The concentration of a particular component in a blood sample, such as glucose, is measured by e.g. an electrode method. In the electrode method, an electrode is brought into contact with a blood sample, and information correlating with the glucose concentration in the blood sample is obtained as an output from the electrode. Based on the output data, the glucose concentration is calculated. Generally, electrode methods are categorized into an equilibrium point method (end point assay) and a differential method (rate assay). In the equilibrium point method, the glucose concentration is computed based on the constant equilibrium value to which the output from the electrode asymptotically approaches. In the differential method, the glucose concentration is computed based on the extreme obtained from the n-th derivative (n is a positive integer) of the output.

It is known that, when whole blood containing blood cells is used as a blood sample in a typical electrode method, the measurement result tends to be lower than the actual value due to the influence of the blood cells. Therefore, to measure the glucose concentration in blood, blood plasma (or blood serum) obtained by removing blood cells from whole blood by centrifugal separation is used as a blood sample. This method, however, is disadvantageous in that the centrifugal separation is necessary for preparing a blood sample, which makes the operation complicated, and that the time taken for the measurement operation, including the preparation of a blood sample, is long. To solve these problems, a method has been proposed in which calculations by the equilibrium point method are correlated with the calculations by the differential method (See Patent Documents 1-3 below).

The method disclosed in Patent Document 1 is conceived based on the fact that, when diluted whole blood is used as a blood sample, the apparent dilution ratio differs from the actual dilution ratio due to the existence of blood cells. This method is based on the assumption that, when diluted whole blood is used as a blood sample, the amount of glucose diffused from within blood cells to the outside before the output corresponding to the maximum is obtained is negligibly small. In the methods disclosed in Patent Documents 2 and 3, the total amount of glucose diffused to the outside of blood cells before the output corresponding to the maximum is obtained is taken into consideration in computing the glucose concentration by the differential method. The total amount of glucose diffused to the outside of the blood cells is related to the hematocrit (proportion of blood cells).

The above-described methods are conceived by attributing the inaccuracy of measurements to the hematocrit and trying to establish a computation technique which is most unlikely to be influenced by the hematocrit. As a result, in the conventional methods, when the glucose concentration in blood is relatively low (e.g. 400 mg/dL or lower), the correlativity with the glucose concentration measured using blood plasma (or blood serum) is improved. However, when the glucose concentration in blood is relatively high (e.g. 500 mg/dL or higher), the correlativity with the glucose concentration measured using blood plasma (or blood serum) is low, and the measurements are still tend to be lower. Therefore, in the above-described method, there is room for improvement with respect to the measurement accuracy in a high concentration range and hence with respect to the measurement range.

Patent Document 1: JP-B-H07-37991
Patent Document 2: JP-A-H09-33533
Patent Document 3: JP-A-H09-318634

DISCLOSURE OF THE INVENTION

An object of the present invention is to make it possible to measure the concentration of a particular component (e.g. glucose) in a blood sample containing blood cells accurately even at a high concentration (e.g. about 500 mg/dL in the case of glucose), without conducting troublesome work such as centrifugal separation and to secure a wide measurement range.

In trying to solve the above-described problems, the inventors found that the concentration of a particular component in a blood sample (e.g. whole blood) containing blood cells can be represented by an expression which is unrelated to the proportion of blood cells in a blood sample, and which is obtained by causing the target concentration to be correlated to a concentration computed by the differential method and a concentration computed by the equilibrium point method.

According to a first aspect of the present invention, there is provided a method for measuring the concentration of a particular component in a blood sample containing blood cells, the method including a computation step of computing the concentration of the particular component based on a variable correlated with the concentration of the particular component. The computation step comprises computing the concentration of the particular component using a relational expression of a concentration (S) in blood plasma obtained by removing blood cell components from the blood sample, a concentration (DI) in the blood sample computed by a differential method and a concentration (EP) in the blood sample computed by an equilibrium point method. The relational expression does not include proportion of the blood cell components in the blood sample as a variable.

For instance, the relational expression is obtained by solving, for the concentration (S) in blood plasma, an expression which correlates the concentration (S) in the blood plasma with a ratio $((S-DI)/(S-EP))$ of a difference $(S-DI)$ to a difference $(S-EP)$. The difference $(S-DI)$ is the difference between the concentration (S) in the blood plasma and the concentration (DI) computed by the differential method, whereas the difference $(S-EP)$ is the difference between the concentration (S) in the blood plasma and the concentration (EP) computed by the equilibrium point method. More specifically, the relational expression is expressed by Equation 2 below, which is obtained by solving Equation 1.

$$(S-DI)/(S-EP)=aS+b, \qquad \text{Equation 1}$$

where a and b each are a constant.

$$S=(-B+\sqrt{(B^2-4aC)})/2a, \qquad \text{Equation 2}$$

where $B=b-aEP-1$, $C=DI-bEP$.

The computation step may comprise a first computation step of obtaining an output correlated with the amount of electron transfer from a detection medium which performs electrontransfer with the particular component, and computing the concentration (EP) of the particular component by the equilibrium point method based on an equilibrium when the output, which changes with time, asymptotically approaches a constant value; and a second computation step of computing the concentration (DI) of the particular component by the differential method based on the maximum of n-th derivative (n is a positive integer, preferably 1 or 2) of a curve representing the change with time of the output before the output reaches the equilibrium.

When the electrode method is employed, the detection medium may be an electrode unit or a biosensor that includes such an electrode unit. When colorimetry is employed, the detection medium may be a color developing material such as pigment. In the electrode method, the output from the detection medium is obtained as a response (e.g. electric physical quantity (such as current)) when stimulation (e.g. electric physical quantity (such as voltage)) is applied to the detection medium. In the colorimetry, the output from the detection medium (color developing material) may be obtained as the amount of reflected light or transmitted light when the detection medium (color developing material) is irradiated with light.

Typically, the concentration measuring method according to the present invention is applicable to the measurement of glucose concentration and also to the measurement of the concentration of other components contained in blood such as potassium ions or LDH (lactate dehydrogenase).

According to a second aspect of the present invention, there is provided a concentration measuring apparatus for measuring the concentration of a particular component in a blood sample containing blood cells. The apparatus comprises a measuring unit for measuring a responsive value reflecting the concentration of the particular component, and a computing unit for computing the concentration of the particular component based on the responsive value. The computing unit computes the concentration of the particular component using a relational expression of a concentration (S) in blood plasma obtained by removing blood cell components from the blood sample, a concentration (DI) in the blood sample computed by a differential method and a concentration (EP) in the blood sample computed by an equilibrium point method. The relational expression does not include proportion of the blood cell components in the blood sample as a variable.

The relational expression may be obtained by solving, for the concentration (S) in blood plasma, an expression which correlates the concentration (S) in the blood plasma with a ratio ((S−DI)/(S−EP)) of a difference (S−DI) to a difference (S−EP). The difference (S−DI) is the difference between the concentration (S) in the blood plasma and the first concentration (DI) computed by the differential method, whereas the difference (S−EP) is the difference between the concentration (S) in the blood plasma and the second concentration (EP) computed by the equilibrium point method.

Specifically, the computing unit computes the first concentration (EP) based on an equilibrium when the responsive value asymptotically approaches a constant value, computes the second concentration (DI) based on the maximum of n-th derivative (n is a positive integer) of a curve representing the change with time of the responsive value, and computes the conclusive concentration (S) based on Equation 2, obtained by solving Equation 1 for the concentration (S) in blood plasma.

$$(S-DI)/(S-EP)=aS+b, \quad \text{Equation 1}$$

where a and b each are a constant.

$$S=(-B+\sqrt{(B^2-4aC)})/2a, \quad \text{Equation 2}$$

where $B=b-aEP-1$, $C=DI-bEP$.

As the responsive value, the measuring unit may measure the amount of electron transfer between the particular component and a detection medium. The measuring unit measures the response (current) when stimulation (e.g. potential difference) is applied to the detection medium. Specifically, for instance, the measuring unit includes a sensor portion as the detection medium and a current measuring portion for measuring current as the response.

The concentration measuring apparatus according to the present invention further comprises a preparation vessel for preparing a blood sample by diluting whole blood. When the sensor portion comprises immobilized oxidoreductase, the sensor portion is oriented to an inside of the preparation vessel at least partially.

In the present invention, the term "blood sample" at least includes whole blood, diluted whole blood, supernatant obtained by centrifugal separation of whole blood and diluted supernatant, unless any particular limitation exists.

BEST MODE FOR CARRYING OUT THE INVENTION

Figure 1:
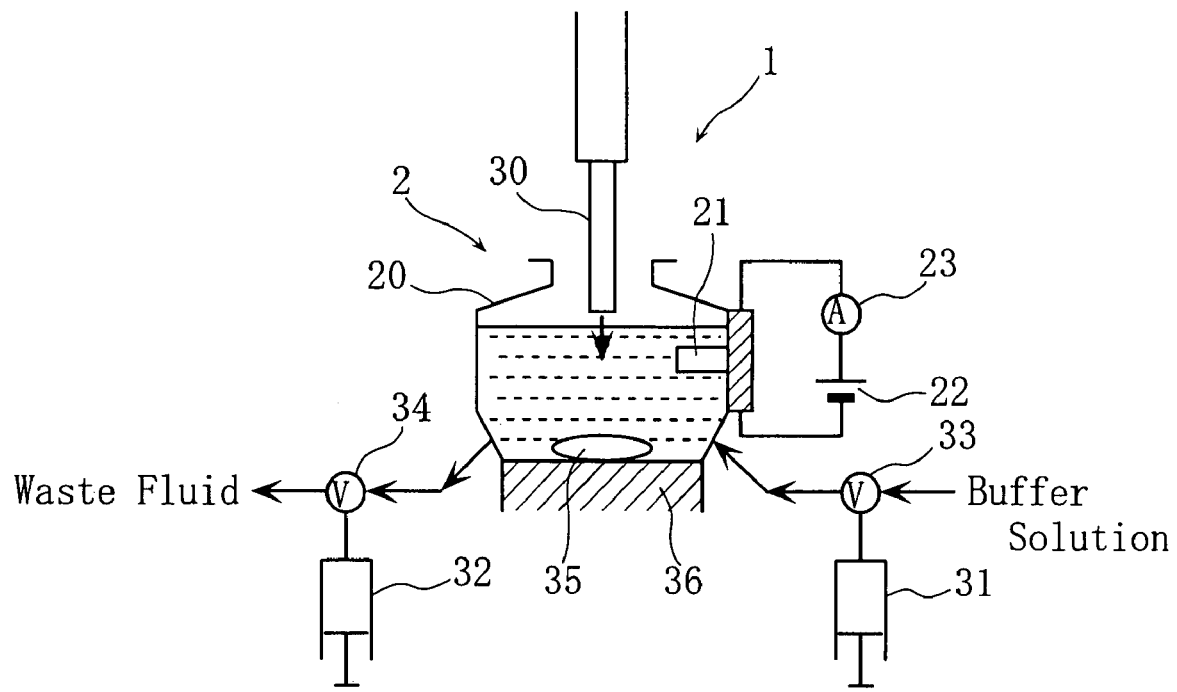
FIG. 1 schematically shows, partially in section, the structure of a glucose measuring apparatus according to the present invention.

The glucose measuring apparatus 1 shown in FIG. 1 is configured to measure the concentration of glucose contained in whole blood by causing a measurement unit 2 to obtain information corresponding to the glucose concentration in a blood sample containing blood cells (diluted whole blood). The measurement unit 2 includes a reaction vessel 20, a sensor 21, a power source 22 and a current measurer 23.

The reaction vessel 23 provides a space in which whole blood is mixed with a buffer solution, thereby preparing a blood sample, while also providing a field for the sensor 21 to come into contact with glucose contained in the blood sample. In the glucose measuring apparatus 1, whole blood and a buffer solution are automatically supplied to the reaction vessel 20, and after the measurement, the blood sample (waste fluid) is discharged from the reaction vessel 20. Specifically, to the reaction vessel 20, a buffer solution is first supplied, and then whole blood is supplied. The supply of whole blood to the reaction vessel 20 is performed through a nozzle 30 of a sampler (not shown). For instance, the supply of whole blood is set to 4 to 20 μL. The supply of a buffer solution to the reaction vessel 20 is performed by utilizing the motive power of a pump 31, whereas the discharge of the waste fluid from the reaction vessel 20 is performed by utilizing the motive power of a pump 32. By opening or closing a valve 33, it is possible to select the state in which the buffer solution can be supplied to the reaction vessel 20 or the state in which the buffer solution cannot be supplied to the reaction vessel. By opening or closing a valve 34, it is possible to select the state in which the waste fluid can be discharged from the reaction vessel 20 or the state in which the waste fluid cannot be discharged from the reaction vessel 20.

An agitator 35 is provided in the reaction vessel 20. The agitator 35 is utilized for stirring and mixing the buffer solution and the whole blood when they are supplied to the reaction vessel 20. The agitator is rotated by a stirrer 36.

The sensor 21 outputs electric physical quantity corresponding to the amount of electron transfer with glucose in the blood sample, and is repetitively usable. Though not shown in the figure, the sensor 21 includes an electrode unit. This electrode unit is exposed to the inside of the reaction vessel 20 and may include an enzyme immobilization layer and electrodes. The enzyme immobilization layer may contain glucose oxidase (GOD) or glucose dehydrogenase (GDH), for example. The arrangement of the electrodes depends on the kind of enzyme contained in the enzyme immobilization layer. For instance, when the enzyme is GOD, the electrodes are configured as a hydrogen peroxide electrode.

The power source 22 is provided for applying a voltage to the electrodes of the sensor 21. The power source 22 may be a direct-current power source, and the voltage to be applied to the electrodes is set to 100 to 500 mV.

The current measurer 23 measures the amount of electron transfer as electric current between the glucose and the electrodes of the sensor 21. When the enzyme is GOD and a hydrogen peroxide electrode is used, glucose is decomposed into gluconic acid and hydrogen peroxide at the enzyme immobilization layer of the sensor 21 due to the action of GOD. Upon application of voltage to the electrodes of the sensor 21, hydrogen peroxide is reduced and decomposed into oxygen and hydrogen ions, donating electrons to the anode. The amount of electrons donated to the anode is measured as current by the current measurer 23. From the time point 0 at which the whole blood is supplied to the reaction vessel 20, the current measured by the current measurer 23 follows the time course as exemplarily shown in FIG. 3.

Figure 2:
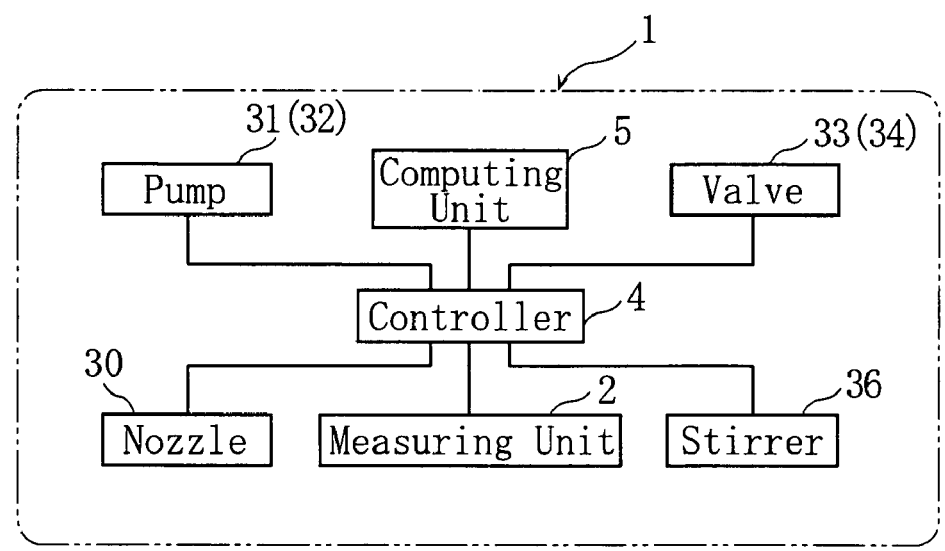
FIG. 2 is a block diagram of the glucose measuring apparatus shown in FIG. 1.

As shown in FIG. 2, the glucose measuring apparatus 1 further includes a controller 4 and a computing unit 5.

The controller 4 controls the operations of various parts. Specifically, the controller 4 controls the movement and operations of the nozzle 30 to suck or discharge the whole blood, the operations of the pumps 31, 32, the opening/closing operations of the valves 33, 34 and the operations of the stirrer 36 (rotation or non-rotation of the agitator 35 (See FIG. 1)). The controller 4 further controls the operations of the measurement unit 2. Specifically, the controller 4 controls the power source 22 shown in FIG. 1 to select the state in which the voltage is applied to the electrodes of the sensor 21 or the state in which voltage is not applied to the electrodes, and controls the current measurer 23 to control the timing at which the current is to be measured. Specifically, for example, the controller 4 controls the measurement operation of the current measurer 23 so that the current is measured repetitively at an interval of 50 to 200 μsec, for example.

The computing unit 5 shown in FIG. 2 computes the glucose concentration in the whole blood based on the measurements obtained at the current measurer 23 (See FIG. 1). The computing unit 5 stores a program necessary for the computation, and the operation of the computing unit is controlled by the controller 4. In this embodiment, the computing unit 5 computes the glucose concentration (S) in the whole blood based on the arithmetic expression given below as Equation 2.

$$S=(-B+\sqrt{(B^2-4aC)})/2a, \quad \text{where} \quad B=b-aEP-1, \quad C=DI-bEP.$$

In Equation 2, a and b each are a constant, EP is a glucose concentration computed by the equilibrium point method, and DI is a glucose concentration computed by the differential method.

In Equation 2, the glucose concentration in a blood sample (e.g. whole blood) containing blood cells is expressed as related to the glucose concentration (DI) computed by the differential method and the glucose concentration (EP) computed by the equilibrium point method, but unrelated to the proportion of blood cells (Hct (%)) in the blood sample. The equilibrium point method and the differential method will be briefly described below, together with the grounds for the appropriateness of Equation 2.

Figure 3:
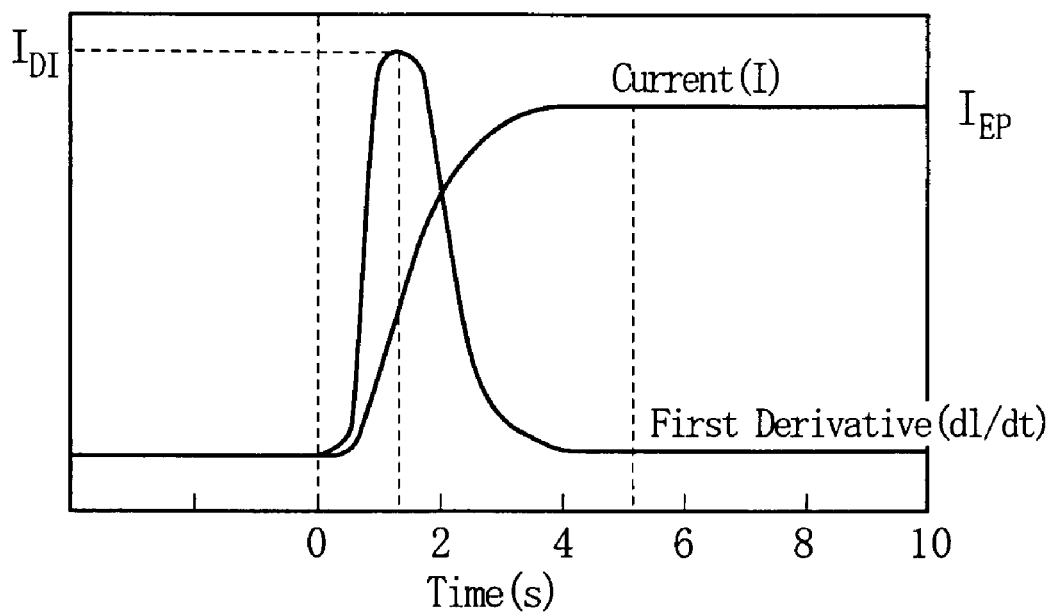
FIG. 3 is a graph showing an example of change with time of current measured by a measurement unit shown in FIGS. 1 and 2 and an example of change with time of the first derivative of the current.

As noted before, at the current measurer 23, the time course of the current as shown in FIG. 3 is observed. Specifically, the current (I) increases from the time point when the whole blood is supplied to the reaction vessel 20 shown in FIG. 1 and asymptotically approaches the equilibrium ($I_{EP}$) after the lapse of a predetermined time period. The magnitude of the equilibrium ($I_{EP}$) is correlated with the glucose concentration in the sample. Therefore, by checking a calibration curve representing the relationship between the equilibrium ($I_{EP}$) and the glucose concentration in advance, the glucose concentration (EP) can be determined based on the equilibrium ($I_{EP}$). This is the equilibrium point method. On the other hand, in the differential method, the glucose concentration is determined based on the maximum when the time course of the current is differentiated n times. For instance, the time course of the first derivative (dI/dt) is shown in FIG. 3. The maximum ($I_{DI}$) of the time course corresponds to the maximum rate of change of the current (I), i.e., the maximum initial reaction velocity. This maximum is correlated with the glucose concentration. Therefore, in the differential method, the glucose concentration (DI) is determined based on the maximum ($I_{DI}$) of the first derivative (dI/dt).

Figure 4:
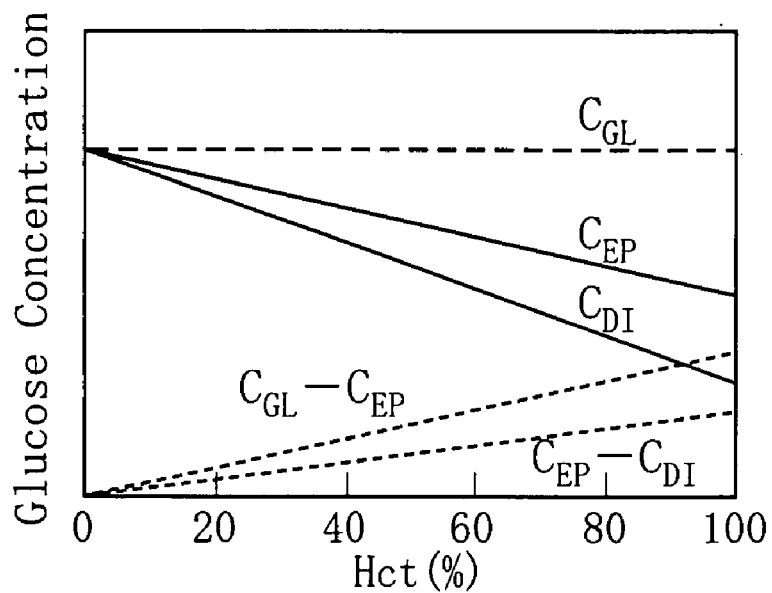
FIG. 4 is a graph showing the relationship between each of blood plasma glucose concentration ($C_{GL}$), a glucose concentration ($C_{EP}$) computed by the equilibrium point method and a glucose concentration ($C_{DI}$) computed by the (first) differential method, and the hematocrit (Hct).

FIG. 4 shows an example of relationship between the hematocrit (Hct (%)) and the glucose concentration ($C_{EP}$) computed by the equilibrium point method and the glucose concentration ($C_{DI}$) computed by the differential method, which are obtained with respect to a plurality of blood samples which are equal to each other in glucose concentration ($C_{GL}$) in the blood plasma state (hematocrit (Hct)=0 (%)) and differ from each other in Hct (%) (See Patent Documents 1 and 2). The glucose concentration ($C_{GL}$) in the blood plasma state (Hct=0(%)) is also shown in FIG. 4.

As will be understood from FIG. 4, as the Hct (%) increases, both of the glucose concentration ($C_{EP}$) computed by the equilibrium point method and the glucose concentration ($C_{DI}$) computed by the differential method linearly reduce, and the deviations (($C_{GL}-C_{DI}$), ($C_{GL}-C_{EP}$)) from the glucose concentration ($C_{GL}$) in the blood plasma state (Hct=0 (%)) linearly increase. Therefore, the ratio (($C_{GL}-C_{DI}$)/($C_{GL}-C_{EP}$)) of the deviation ($C_{GL}-C_{DI}$) of the glucose concentration ($C_{DI}$) by the differential method from the glucose concentration ($C_{GL}$) in the blood plasma state to the deviation ($C_{GL}-C_{EP}$) of the glucose concentration ($C_{EP}$) by the equilibrium point method from the glucose concentration ($C_{GL}$) in the blood plasma state is constant and unrelated to Hct (%) when the glucose concentration ($C_{GL}$) in the blood plasma state is the same.

Although shown in FIG. 4 are the results of measurement with respect to blood samples having a same glucose concentration ($C_{GL}$(=constant)), the above-described relationship of the ratio of deviation (($C_{GL}-C_{DI})/(C_{GL}-C_{EP}$)) holds true for any glucose concentration as long as the glucose concentration ($C_{GL}$) of the blood samples (in blood plasma) is equal.

On the other hand, with respect to different glucose concentrations in blood plasma, the inventors of the present invention have studied the relationship between the ratio of deviation and the glucose concentration in blood plasma. Specifically, with respect to a plurality of whole blood samples of different glucose concentrations, the glucose concentration (DI, EP) was measured by the (first) differential method and the equilibrium point method, and the glucose concentration (S) in the blood plasma obtained by centrifugal separation was also measured. Then, the ratio of deviation (S–DI)/(S–EP)) was computed based on the measurements of the glucose concentrations. The results are shown in FIG. 5.

It is to be noted that the current values necessary for the computation of the glucose concentration (DI) by the differential method, the glucose concentration (EP) by the equilibrium point method and the glucose concentration (S) in the blood plasma were grasped based on the current values obtained in a full-automatic glucose test meter "GA-1160" (available from ARKRAY Inc.)

Figure 5:
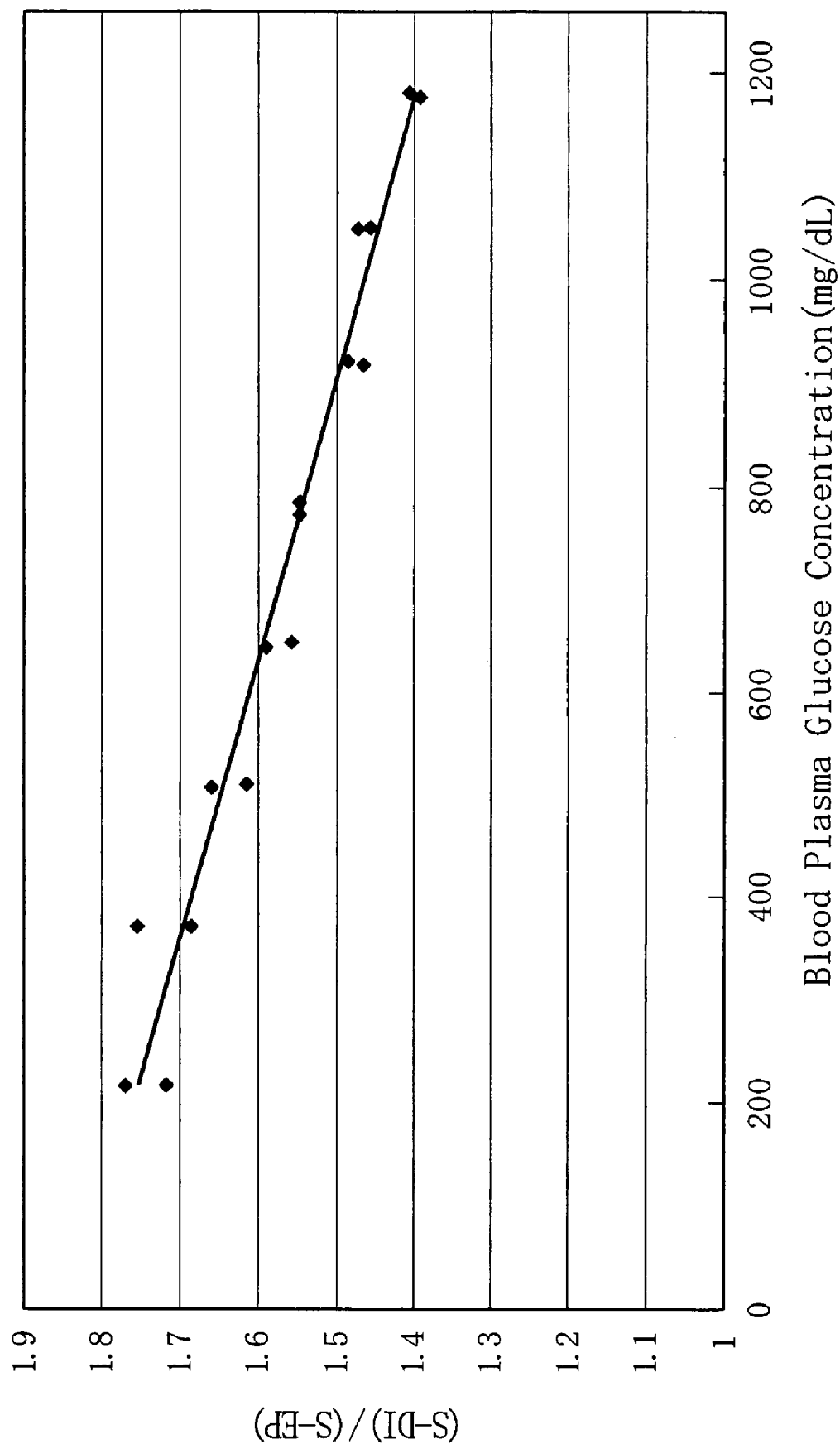
FIG. 5 is a graph showing the results of study of relationship between the glucose concentration in blood plasma and the ratio of deviation of a glucose concentration computed by the differential method and a glucose concentration computed by the equilibrium point method from the glucose concentration in blood plasma.

As will be understood from FIG. 5, in the measurement range, the above-described ratio of deviation ((S–DI)/(S–EP)) changes within the range above 1 and reduces linearly as the glucose concentration (S) in blood plasma increases. This result indicates that, as the glucose concentration (S) in blood plasma increases, the deviation of the glucose concentration (DI) by the differential method from the glucose concentration (S) in blood plasma reduces by a larger amount as compared with the glucose concentration (EP) by the equilibrium point method. Further, it is also indicated that the ratio of deviation ((S–DI)/(S–EP)) can be approximated by a linear function of the glucose concentration (S) in the blood plasma state, as given as Equation 1 below.

$(S-DI)/(S-EP)=aS+b$, where a and b each are a constant.

Herein, when the plot points of FIG. 5 is subjected to linear approximation by the method of least squares, a=–0.00037 and b=1.83130.

When the Equation 1 is solved for the glucose concentration (S) in blood plasma, the above-described Equation 2 is obtained.

According to the present invention, by relating the glucose concentration (S) in the blood plasma state to the glucose concentration computed by the differential method and that computed by the equilibrium point method, the arithmetic expression (Equation 2) to be employed at the computation unit 5 is obtained as an equation which is unrelated to the hematocrit (Hct (%)). Therefore, according to the present invention, the accurate concentration measurement is possible regardless of the hematocrit (Hct (%)) and even with respect to a blood sample in a relatively high concentration range (500 to 10000 mg/dL). Therefore, a wide measurement range can be secured. This point will be clear from the example given below.

EXAMPLE

Hereinafter, it will be demonstrated that the glucose concentration computed by the Equation 2 is properly correlated with the glucose concentration in blood plasma even when the glucose concentration lies in a relatively high concentration range (500 to 12000 mg/dL) and that the measurement range can be increased by employing the computation method utilizing the Equation 2.

In this example, with respect to each of a plurality of whole blood samples of different glucose concentrations, the glucose concentration was computed by the Equation 2 (inventive arithmetic expression), by the Equation 3 given below (conventional arithmetic expression) and by the equilibrium point method. With respect to a and b in the Equation 2, the values obtained by the measurements shown in FIG. 5 (a=–0.00037, b=1.831309) were used. In the Equation 3 given below, $K_1$=0.68 and $K_2$=5.07.

$S=EP+K_1\times(EP-DI)+K_2$.    Equation 3

As a reference, the glucose concentration of each of the above-described whole blood samples in the blood plasma state obtained by centrifugal operation was measured as well. The glucose concentration in the blood plasma state was measured by using a full-automatic glucose test meter "GA-1160" (available from ARKRAY Inc.). The equilibrium ($I_{EP}$) of current values necessary for the computation by the Equation 2 (inventive arithmetic expression), the Equation 3 (conventional arithmetic expression) and the equilibrium point method, and the maximum ($I_{DI}$) when the measured current is differentiated once were grasped based on the current measured with respect to the above-described whole blood samples by using a full-automatic glucose test meter "GA-1160" (available from ARKRAY Inc.).

Figure 6:
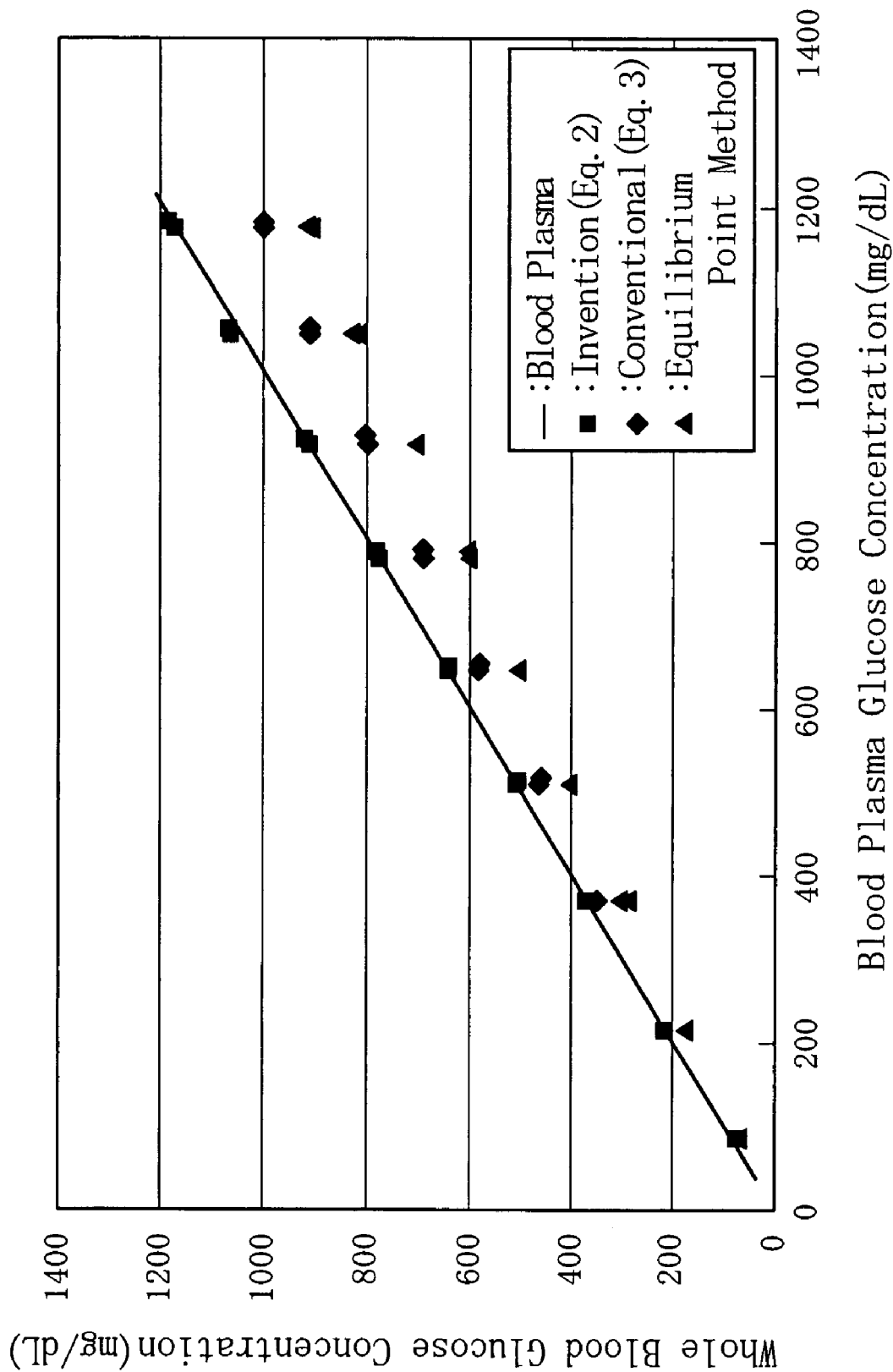
FIG. 6 is a graph showing the correlativity of the glucose concentrations computed by each of the arithmetic expressions with the glucose concentration in blood plasma.

FIG. 6 shows the measurements obtained by each of the measurement techniques. As will be understood from the figure, the glucose concentration computed by the equilibrium point method deviates largely from the glucose concentration in blood plasma. As compared with the glucose concentration computed by the equilibrium point method, the glucose concentration computed based on the Equation 3 (conventional arithmetic expression) is more correlated with the glucose concentration in blood plasma. However, the glucose concentration based on the Equation 3 deviates from the glucose concentration in blood plasma in a high concentration range (higher than 400 mg/dL), and the degree of deviation increases as the glucose concentration increases.

On the other hand, the glucose concentration computed based on the Equation 2 (inventive arithmetic expression) is highly correlated with the glucose concentration in blood plasma, including the high concentration range (500 to 12000 mg/dL). Therefore, by computing the glucose concentration based on the Equation 2 (inventive arithmetic expression), the measurement accuracy in a high concentration range is enhanced, whereby a wide measurement range can be secured.

The present invention is not limited to the foregoing embodiment and may be varied in various ways. For instance, although the ratio of deviation (S–DI)/(S–EP) is correlated with the glucose concentration (S) in blood plasma as a linear function in the foregoing embodiment, it may be correlated as another function.

In the above-described glucose measuring apparatus 1, the sensor 21 of the measurement unit 2 is structured to be used repetitively by the electrode method. However, the structure for obtaining the output correlated with the glucose concentration in a blood sample is not limited to that of the above-described measurement unit 2. For instance, the present invention is also applicable to the glucose concentration measurement using a disposable glucose sensor and the glucose concentration measurement utilizing colorimetry. Further, the present invention is applicable to the measurement of the concentration of a component in blood other than glucose.

The invention claimed is:

1. A method of determining the concentration of a particular component in a blood sample, comprising:
    (1) determining a calibration curve for a measuring device by
        (a) analyzing a blood sample that has a known concentration of the component using an electrode specifically sensitive to the component,
        (b) obtaining a time series of outputs from the electrode,
        (c) calculating an apparent component concentration at the time of equilibrium as measured by the electrode,
        (d) computing the concentration at which the first or second derivative of the time series reaches a maximum,
        (e) generating a set of calibration data by repeating steps (a)-(d) with samples of varying known component concentrations,
        (f) and fitting the resulting calibration data to the relational expression $((S-DI)/(S-EP))=a \times S+b$, wherein
            (i) S is the known concentration of the component in the sample,
            (ii) DI is the concentration at which the derivative reaches the maximum,
            (iii) EP is the apparent component concentration at the equilibrium point,
            (iv) a and b are parameters calculated by least-squares fitting; and
        (g) storing a and b as calibration parameters in the measuring device; and
    (2) using the calibrated measuring device to
        (a) analyze a blood sample that has an unknown concentration of the component using an electrode specifically sensitive to the component,
        (b) obtain a time series of outputs from the electrode,
        (c) calculate an apparent component concentration at the time of equilibrium as measured by the electrode,
        (d) compute the concentration at which the first or second derivative of the time series reaches a maximum,
        (e) solve the expression $((S-DI)/(S-EP))=a \times S+b$ for S, wherein
            (i) DI is the concentration at which the derivative reaches the maximum,
            (ii) EP is the apparent component concentration at the equilibrium point,
            (iii) a and b are the stored calibration parameters, and
            (iv) S is the concentration of the component in the sample; and
        (f) calculate the true concentration of component in the blood sample.

2. The method according to claim 1, wherein each of the outputs from the electrode is an electric current when a voltage is applied to the electrode.

3. The method according to claim 1, wherein the blood sample is diluted whole blood.

4. The method according to claim 1, wherein the particular component is glucose.

5. An apparatus for determining the concentration of a particular component in a blood sample, comprising:
    (1) an electrode that is specifically sensitive to the particular component in the blood sample,
    (2) a measuring unit that measures a plurality of time series of outputs from the electrode,
    (3) a computing unit that has a stored program that comprises executable instructions for performing the following steps:
        (a) calculating the apparent component concentration at the time of equilibrium of a time series of measurements from the blood sample,
        (b) determining the concentration at the point at which the first or second derivative of a time series reaches a maximum,
        (c) generating calibration parameters a and b in the expression $((S-DI)/(S-EP))=a \times S+b$, wherein
            (i) DI is the concentration at which the derivative reaches the maximum,
            (ii) EP is the apparent component concentration at the equilibrium point, and
            (iii) S is the concentration of the component in the sample
        (d) storing the calibration parameters; and
    (4) a control unit that connects the measuring unit and the computing unit.

6. The apparatus according to claim 5, further including a sensor portion for performing electron transfer with the particular component, and a current measuring portion for measuring current.

7. The apparatus according to claim 6, wherein the sensor portion comprises an immobilized oxidoreductase.

8. The apparatus according to claim 6, further comprising a preparation vessel for preparing the blood sample by diluting whole blood, wherein the sensor portion is located at least partially inside the preparation vessel.

9. The apparatus according to claim 5, wherein the particular component is glucose.

* * * * *